(12) United States Patent
Thomsen

(10) Patent No.: US 9,357,927 B2
(45) Date of Patent: Jun. 7, 2016

(54) DENTAL ABUTMENT FOR ORAL SCANNING

(75) Inventor: Christian Schärfe Thomsen, Copenhagen N (DK)

(73) Assignee: Elos Medtech Pinol A/S, Gorlose (DK)

(*) Notice: Subject to any disclaimer, the term of this patent is extended or adjusted under 35 U.S.C. 154(b) by 0 days.

(21) Appl. No.: 14/005,779

(22) PCT Filed: Mar. 16, 2012

(86) PCT No.: PCT/DK2012/050082
§ 371 (c)(1), (2), (4) Date: Sep. 17, 2013

(87) PCT Pub. No.: WO2012/126475
PCT Pub. Date: Sep. 27, 2012

(65) Prior Publication Data
US 2014/0011155 A1   Jan. 9, 2014

Related U.S. Application Data

(60) Provisional application No. 61/454,194, filed on Mar. 18, 2011.

(30) Foreign Application Priority Data

Mar. 18, 2011  (EP) ..................................... 11158868

(51) Int. Cl.
*A61C 9/00* (2006.01)
*A61B 5/00* (2006.01)
*A61C 8/00* (2006.01)

(52) U.S. Cl.
CPC ............. *A61B 5/0088* (2013.01); *A61B 5/0062* (2013.01); *A61C 8/00* (2013.01); *A61C 8/0001* (2013.01); *A61C 9/004* (2013.01)

(58) Field of Classification Search
CPC .......... A61C 9/004; A61C 8/00; A61C 8/005; A61B 5/0062
USPC .................................. 433/29, 173–176, 201.1
See application file for complete search history.

(56) References Cited

U.S. PATENT DOCUMENTS 5,259,759 A *  11/1993  Jorneus et al. ................. 433/173
6,283,752 B1 *  9/2001  Kumar .......................... 433/172

(Continued)

FOREIGN PATENT DOCUMENTS

EP    0 867 153 A1   9/1998
EP    1 310 217 A2   5/2003

(Continued)

OTHER PUBLICATIONS

I Weiland, "Zenotec CAD/CAM titanium bases", CE 0483, 530087e. 00.12/09.

*Primary Examiner* — Cris L Rodriguez
*Assistant Examiner* — Hao D Mai
(74) *Attorney, Agent, or Firm* — Foley & Lardner LLP

(57) ABSTRACT

A scan body element is configured to be inserted in a dental implant or implant analog for scanning with or in an optical scanning system. The scan body element has a top part with at least one geometric feature recognizable via scanning. A metallic lower part is shaped to fit to a dental implant or an analog, and fixed to the top part. A central part is arranged inside the lower part, and includes a threaded portion and a recess for receiving a screw driver through a hole in the top part. The recess allows the threaded portion to be turned relative to the lower part to fasten the scan body element to the implant or the analog. The central part is configured to be interlocked between the lower part and the top part such that the scan body element is arranged as a single element.

18 Claims, 5 Drawing Sheets

(56) References Cited

U.S. PATENT DOCUMENTS

| | | | |
|---|---|---|---|
| 6,488,501 B1* | 12/2002 | Harding | 433/173 |
| 6,769,913 B2* | 8/2004 | Hurson | 433/173 |
| 6,824,386 B2* | 11/2004 | Halldin et al. | 433/173 |
| 7,066,736 B2* | 6/2006 | Kumar et al. | 433/173 |
| 8,002,547 B2* | 8/2011 | Porter et al. | 433/173 |
| 8,007,279 B2* | 8/2011 | Bassett et al. | 433/173 |
| 8,419,429 B2* | 4/2013 | Wang | 433/173 |
| 2002/0039717 A1* | 4/2002 | Amber et al. | 433/172 |
| 2006/0019219 A1 | 1/2006 | Saliger et al. | |
| 2006/0105296 A1* | 5/2006 | Linder et al. | 433/173 |
| 2008/0176188 A1 | 7/2008 | Holzner et al. | |
| 2012/0214130 A1* | 8/2012 | Krivoruk | 433/173 |
| 2012/0295226 A1* | 11/2012 | Robb et al. | 433/201.1 |
| 2013/0196290 A1* | 8/2013 | Herrington et al. | 433/173 |

FOREIGN PATENT DOCUMENTS

| | | |
|---|---|---|
| EP | 2 130 514 A1 | 12/2009 |
| WO | WO-2010/091868 A1 | 8/2010 |

* cited by examiner

DENTAL ABUTMENT FOR ORAL SCANNING

CROSS-REFERENCE TO RELATED APPLICATIONS

This application is a national phase of international application PCT/DK2012/050082, filed Mar. 16, 2012, which was published on Sep. 27, 2012, as WO 2012/126475, which claims the benefit of EP application No. 11158868.7 and U.S. provisional application No. 61/454,194, both of which were filed Mar. 18, 2011. The respective contents of each of these applications are incorporated here by reference in their entirety.

FIELD OF THE INVENTION

The invention relates to the field of devices for implantation. More specifically, the invention provides a scan body element or scanning abutment for dental implants which is suited for high precision inter-oral scanning while mounted on a dental implant. However, the scan body element is also suited for extra-oral scanning when mounted on an implant analog, e.g. mounted in a mould of the patient's mouth.

BACKGROUND OF THE INVENTION

Custom made dental abutments, such as crowns or bridges for mounting on an implant fastened in the jaw bone of a patient, are commonly manufactured based on a scanning. A scanning is performed of a scan body element or scanning abutment mounted on an implant analog in a mould of the patient's mouth, i.e. outside the patient's mouth. Alternatively, the scanning can be performed in the mouth of the patient with the scan body element mounted on an implant which has been implanted in the jaw bone of the patient, i.e. inter-orally. The scanning of a recognizable feature on a surface of the scan body element serves to provide a precise information of the position and orientation of the scan body element, and thereby also providing information of the position and orientation of the implant or implant analog, so as to enable manufacturing of a custom abutment that fits precisely onto the implant.

A known scan body element includes a threaded base part which is screwed onto the implant. Once the base part has been fastened to the implant analog, the dentist or surgeon manually positions and presses a polymeric cap onto an upper portion of the base part. The polymeric cap has features recognizable in a subsequent scanning. An example of such scan body element is shown in EP 2 130 514 A1.

However, it appears that this system provides a rather poor precision in the scanning result with respect to the orientation of the implant, as the scan element is mounted on a further part screwed into the implant, thus introducing a possible error in determination of tilt angle of the implant. Therefore, the resulting dental bridge or bar manufactured based on such scan may suffer from imprecise fitting onto the implant which may cause various health problems, e.g. infections and bone deterioration, thus providing additional costs and pain for the patient. In general, a very high precision is required, down to a tolerance less than e.g. 5-6 μm.

Furthermore, it can be a rather cumbersome process to fasten each part necessary to do the scan individually on the implant, especially when the scanning is performed inter-orally.

SUMMARY OF THE INVENTION

Thus, according to the above, it is an object of the present invention to provide a scan body element which is capable of providing more precise scanning results, thus allowing manufacturing of dental products with better fitting to an implant.

It is also an object to provide a simplified method of placing the scan body element in the implant to be measured to further ensure precise scanning results.

In a first aspect, a scan body element being insertable in, or on, a dental implant, or in, or on, an implant analog, and recognizable in, or with, an optical scanning system arranged for finding orientation and position of the scan body element is provided, the scan body element comprising:
  a top part comprising at least one geometric feature recognizable in the optical scanning system, the top part being made of a non-metal material, such as a polymer or a ceramic,
  a lower part made of a metal or metal alloy and shaped to fit to a dental implant or an implant analog, wherein the lower part is fixed to the top part, and
  a central part arranged in a central opening of the lower part, wherein the central part comprises a threaded portion, and a recess for receiving a screw driver through the top part, so as to allow the threaded portion to be turned relative to the lower part in order to fasten the scan body element to the dental implant or the implant analog.

It is understood that the scan body element can be inserted directly in or on an implant, directly in or on an implant analog. However, in some cases, the scan body element may be inserted in or on an intermediate structure, e.g. an abutment mounted in or on the implant or implant analog.

Such scan body element is advantageous, since it allows a precise scanning result. This is obtained because the central threaded part can be turned relative to the lower part, and because the top part is fixed to the lower part. Thus, the lower part that fits to the implant or implant analog is fixed to the top part, and thus also to the geometric feature recognized in the scanning, thereby providing a high precision in orientation of the geometric feature relative to the implant or implant analog. The result is a precise scanning result with a high precision of the determined tilt angle of the implant. The precision that can be obtained with such scan body element is superior to prior art solutions where a top cap is mounted with an inevitable lack of precision due to manual fitting onto the lower part, which has been fastened to the implant or implant analog. A tilt between top cap and lower part will result in a non-precise determination of tilt angle of the implant relative to its surroundings.

Furthermore, the scan body element is highly suited in versions that allow inter-oral scanning, i.e. scanning in the patient's mouth after the scan body element has been fastened to the implant. E.g. the lower and central parts can be made of titanium, while the top part is made of a polymer or ceramic which is accepted for inter-oral use. The fact that the design allows one single assembly for mounting on the implant or implant analog by means of a screw driver, provides an easy mounting which is especially important for inter-oral use. The dentist or surgeon only has to handle one single element in the patient's mouth, rather than first fastening a first element to the implant, and subsequently having to press a second element onto the first element. Hereby, the risk of dropping an element in the patient's mouth is reduced. The inter-oral use is further supported by the high orientation precision which enables a limited total height of the scan body element, and the scan body element may be shaped so as to provide a height of 8-10 mm.

Still further, the scan body element can be made in different versions that each fits to a specific size or type of implant, and still the same central part recess can be used for all versions, thus allowing one single screw driver to be used for all versions regardless of which type or size the scan body element fits to. This saves confusions and costs related to different screw drivers in a system with several size and type versions. A color code on an exterior surface part of the scan body element can be used to indicate the size and type of the scan body.

The recess in the central part may be shaped to fit a specially designed screw driver tool that may be designed to apply a limited torque, so as to avoid problems with a too tight fitting during mounting of the scan body element.

A lower part made of metal provides a durable scan body element, since the lower part is the one being in contact with the implant or implant analog and thus wear is expected on this part, while the top part of non-metal, such as polymer or ceramic, provides advantageous scanning properties that cannot be obtained by metal, not even by the use of paint or coating.

To allow easy use without confusions, in one embodiment at least one of the top part, the lower part, and the central part, have a visible colored area, wherein the color of the colored area is arranged to inform a user which type or size of implant or implant analog the scan body element fits onto, or which scanning system the scan body element can be scanned in. This allows production of sets with many different scan body elements that each fits onto a specific type or size of implant, and/or type of scanner. Especially, the recess in the lower part may in all versions of the scan body element of such set have the same shape, thus allowing one single type of screw driver to be used for all versions of scan body elements in the set.

In one embodiment, the top part and preferably also the lower part comprise openings arranged for insertion of a screw driver, so as to allow the screw driver to be received in said recess of the central part. Especially, the top part may be a solid polymer element in which its upper portion provides an orifice through which the screw driver is guided to the recess in the central part.

The central part may be displaceable relative to the lower part along a longitudinal axis. Especially, the central part may be a screw with a head with a screw driver recess in one end and with a threaded opposite end. Such screw is preferably interlocked in the lower part, displaceable in a limited distance, e.g. 1-2 mm, limited in a longitudinal direction by the top part. Especially one screw head can be used for multiple scan body elements each fitted to different types and sizes of implants or implant analogs. Hereby only one single screw driver is necessary.

The top part is preferably locked in position relative to the lower part by means of at least one of: 1) one or more exterior protrusions on the lower part arranged for being press fitted inside the top part, 2) by means of glue, 3) by means of co-moulding, 4) by means of corresponding threads on the top part and the lower part, and 5) by means of a shrinking process. By the term 'locked in position' means that the top part fits so tight to the lower part, or in other ways is fixed in position relative to the lower part such that it does not move relative to the lower part, during normal use, i.e. in a dental clinic or the like. Hereby an efficient position and orientation locking between the lower part and the top part is provided, thus ensuring a precise and well-defined orientation of the geometric feature on the top part relative to the implant or implant analog. It is understood that the mentioned ways of providing this position locking between top part and lower part are not exhaustive, and other means for providing position locking may be used, such as known by the skilled person.

In preferred embodiments, the top part is a solid polymer element. Especially, the lower part may comprise at least one circumferential protrusion arranged to provide a press fitting to an inner portion of the top part.

In one embodiment, the top part, the lower part and the central part are assembled together so as to constitute one single element when fastening the element to the implant or the implant analog. E.g. the central part can be a screw with a head in an upper end which together with the lower part and top part interlocks the screw. Thus, for normal use, the operator does not need to assembly the scan body element from two or more single elements that may cause confusion or even errors.

The top part may have an optical scanning recognizable portion with respect to an angular position by having a cross-sectional planar first surface with respect to the longitudinal axis of the scan body element. Such planar first surface is preferably placed on an upper part of the top part. A second planar surface may also be present on another part of the top part so as to improve scanning possibilities.

In preferred embodiments, the top part preferably surrounds an upper portion of the lower part. Hereby a good and tight fit between the top part and the lower part can be provided, so as to prevent any relative moving or tilting between these two parts, thereby providing a precise match between position and orientation of geometric features for scanning and the implant or implant analog. Especially, a length of the upper portion of the lower part being surrounded by the top part may be at least 20% of an outer height of the top part. Most preferably, a rather large portion of the top part is internally supported by the lower part structure, thus preventing a relative tilt between top part and lower part. The percentage may be significantly higher than 20%, such as at least 30%, such as at least 40%, such as at least 50%, such as at least 60%, such as at least 70%, such as at least 80%, or such as at least 90%. Especially, this percentage may be selected to be high for embodiments suited for mounting on implants or implant analogs with male interfaces. Such scan body elements may typically have a top part which fully surrounds the lower part, such that only a lower part of the central part protrudes from the top part. In embodiments suited for mounting on implants or implant analogs with female interfaces, the percentage may be selected lower, since here the lower part typically protrudes from the top part which only surrounds an upper portion of the lower part.

A total outer height of the scan body element above the implant or implant analog is preferably selected to be low enough to allow inter-oral use, i.e. low enough to allow practical handling of the screw driver inter-orally during mounting. E.g. the total outer height may be below 15 mm, when the scan body element is mounted on the implant or implant analog. For use on an implant analog in a mould, the total outer height may not be important, but for practical inter-oral use, it is preferred that the height is limited so as to allow space for the operator to mount and fasten the scan body element in the patient's mouth.

The lower part preferably surrounds an upper portion of the central part. Especially, an inner surface of the lower part and an outer surface of the upper portion of the central part are shaped such that the central part provides a self-centering effect upon being screwed onto the implant or implant analog. Hereby, the lower part fits precisely on the implant or implant analog without any tilting. In specific embodiments, a length of the upper portion of the central part being surrounded by the lower part is at least 40% of an outer height of the lower part, such as at least 50%, such as at least 60%, such as at least 70%, such as at least 80%, such as at least 90% or even more, when the scan body element is fastened to the implant or the analog. Especially, it may be preferred that the lower part surrounds the central part such that even the upper most part of the central part is surrounded by the lower part when the central part is pushed upwards to ensure that the lower part can engage with the engaging part of the implant or implant analog without the operator having to turn the thread of the central part in the corresponding thread of the implant or implant analog. This facilitates practical mounting of the scan body element, and this is especially important in case of inter-oral mounting.

The top part is preferably made of one of: 1) a polymer comprising PEEK, 2) a ceramic, 3) Teflon®, and 4) POM. E.g. a polymer comprising at least 95% PEEK may be preferred. However, other bio-compatible non-metallic materials known by the skilled person may also be used so as to enable the scan body element to be used inter-orally. The top part is preferably manufactured by means of moulding or turning.

The lower part is preferably made of a metal or an alloy comprising at least one of: Ti, Zr, and steel. Alternative metals to be used may be found in ISO 5832. Especially, pure titanium may be used. The central part is preferably also made of a metal or alloy, such as pure titanium. The lower part may be manufactured by mill-turning. The central part may also be manufactured by mill-turning. The lower part may be coloured by a suitable process, electrochemically, physical vapour deposition (PVD), or other surface treatments, with bio-compatibility for inter-oral use.

The scan body element may be made from bio-compatible materials and arranged for inter-oral use. Especially, the scan body element is made from materials certified for inter-oral use according to standards in force.

It is appreciated that the mentioned embodiments may in any way be combined with each other.

BRIEF DESCRIPTION OF DRAWINGS

In the following, the invention will be described in more detail by referring to embodiments illustrated in the accompanying drawings, of which

DETAILED DESCRIPTION OF THE INVENTION

Figure 1:
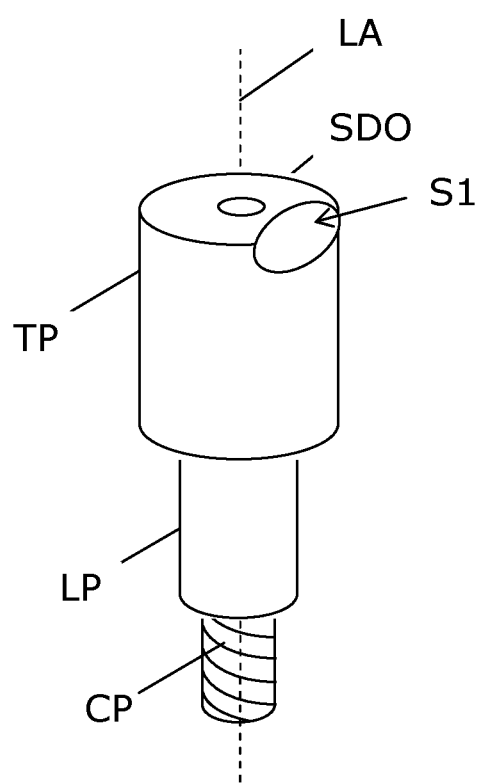
FIG. 1 shows a semi-transparent sketch of a simple scan body embodiment.

FIG. 1 shows the main parts of a simple scan body element assembly which is ready for mounting on an implant analog on a mould of a patient's mouth, or ready for mounting directly in the implant in the patient's mouth. The illustration is a 3D illustration with partly transparent parts that allow visualization of the interior parts of the scan body.

As seen, a top part TP, a lower part LP, and a central part CP with a thread form one single scan body element. This makes the scan body element advantageous for inter-oral use, since the dentist or surgeon only has to handle one single element in the patient's mouth, rather than first fastening a fastening element to the implant, and subsequently having to press a top cap onto the fastening element, as in the prior art. Hereby, there are two separate elements that may be accidentally dropped in the patient's mouth. This risk has been reduced by providing one single scan body element.

The top part TP is preferably made of a polymer, e.g. PEEK, or at least including PEEK. Most preferably the top part TP is a solid polymer element turned into shape so as to provide a precise shape. A plane surface S1 provides a geometric feature which is recognizable in a scanning. Preferably, this surface S1 is provided on an upper part of the top part TP and tilted relative to the longitudinal axis LA, such as also shown in FIG. 1.

The top part TP may be press fitted onto the lower part LP so as to provide a tight fit, tight enough to ensure that the top part can be considered completely fixed to the lower part during all normal use, thereby providing a precise scanning result. Preferably, the lower part LP extends inside a significant part of the length of the top part TP, e.g. more than 50% of the height of the top part TP, so as to provide a precise control of the position of the top part TP relative to the lower part LP without any relative tilting. This provides a well-defined position and orientation of the surface S1 relative to the implant or analog, when the scan body is mounted on the implant or analog.

The central part CP has in one end a recess for receiving a screw driver, and in the opposite end the central part CP has a thread arranged for fitting a corresponding thread on an implant or analog. The central part CP is preferably displaceable in a longitudinal direction, i.e. along axis LA, by being shaped to fit inside the lower part, e.g. by means of a clearing providing a rather tight fit thus preventing tilting between the lower part LP and the central part CP, but still enough clearing to allow the central part CP to be turned relative to the lower part LP. In normal use, the central part CP is preferably interlocked by the lower part and the top part, such that the scan body element constitutes one single assembly.

In the illustrated embodiment all three parts are substantially rotational symmetric elements TP, LP, CP around longitudinal axis LA, and the elements may be manufactured by turning processes followed by appropriate treatment, e.g. forming of the surface S1 on the top part TP, forming of protrusions or indentations of the lower part LP arranged engage with corresponding parts on an implant or analog, or forming of a thread on a lower portion of the central part CP.

A centrally placed hole SDO, a screw driver opening, in the top part allows insertion of a screw driver to be received in the recess R in the upper portion of the central part CP, thus allowing turning of the central part CP for fastening the scan body element to the implant or analog. In the illustration, the lower part LP surrounds the upper portion of the central part CP, and thus the lower part LP also has an opening allowing the screw driver to reach the recess R of the central part CP.

Figure 2A:
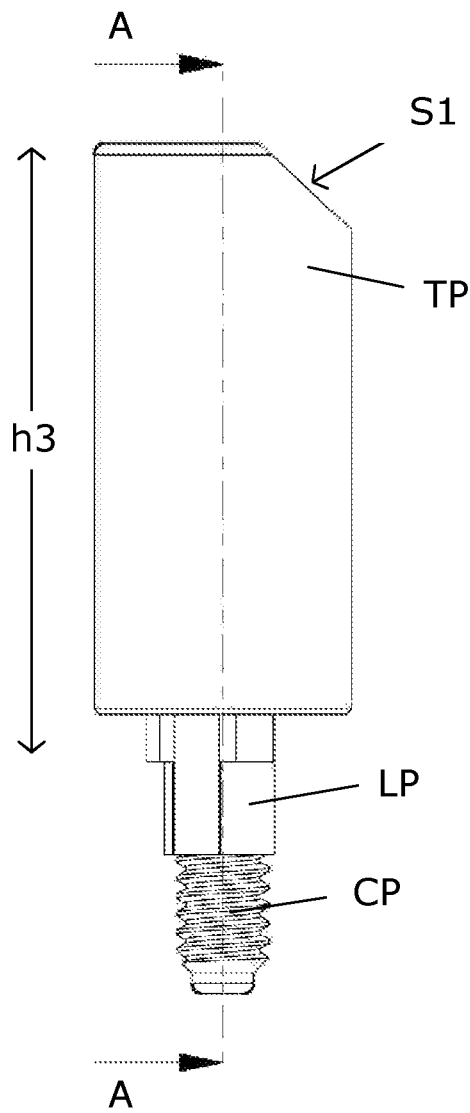
FIGS. 2a and 2b illustrate two views of a scan body embodiment suited for mounting on an implant with a female interface.
Figure 2B:
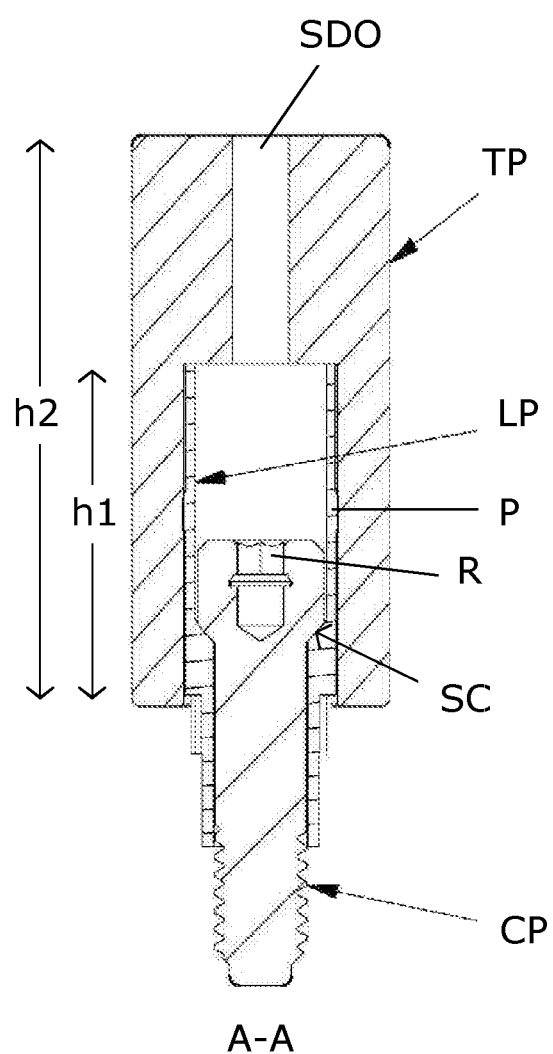

FIGS. 2a and 2b illustrate two views of another embodiment with more details, namely a side view and a section view of an embodiment suited for mounting on an implant or implant analog with a female interface, i.e. with an indentation arranged to engage with the protruding bottom part of the lower part LP of the scan body element. The basic function of the top part TP, the lower part LP, the central part CP, and the recognizable surface S1 has already been described in connection with the embodiment of FIG. 1. Thus, here only specific features of the embodiment will be described.

As seen, the central part has the shape of an ordinary screw with a head in one end, and with a recess R in the upper portion of the head. The head is wider than the lower portion with a thread. Due to the lower internal diameter of the lower end of the lower part LP, being lower than the external diameter of the head of the central CP. The central part CP is longitudinally displaceable inside the lower part LP down to a point, where a downward pointing surface of the head meets an upward pointing surface of the lower part LP. These two surfaces are shaped to fit to each other such that a self-centering effect is provided so as to ensure that the lower part LP will fit precisely onto the implant or analog, when fastened.

The top part TP is substantially cylindrical in shaped from a solid polymer block by mill-turning and subsequent drilling to provide the central screw driver opening SDO. A circumferential protrusion P on a portion of the lower part LP which is placed inside the top part TP serves to provide a tight fit to an inner part of the top part TP after being press fitted inside the top part TP. The clearing between top part TP and lower part LP is so small that the top part TP can be considered completely fixed to the lower part LP for all practical use, once press fitted in place. Before press fitting the top part TP to the lower part LP, the central part is positioned, and once the top part TP has been mounted, the central part is interlocked between the lower part PL and the top part TP, and thus all three parts TP, LP, CP constitute one single assembly for normal use.

The lower part LP preferably extends a distance h1 inside the top part TP which exceeds 50% of a total height h2 of the top part TP, which ensures a high degree of lateral control of the position of the top part TP relative to the lower part LP, thereby preventing relative tilt between these parts TP, LP, which helps to provide a high scanning precision. This percentage may be down to such as 20%, but it may also be preferred to be more than 60%. It is preferred, that the lower part LP extends upwardly such that it surrounds the upper part of the central part CP when it is pressed upwardly to a degree ensuring that the lower part LP can engage with the implant or implant analog interface without the central part having to be turned, thus facilitating practical mounting on the implant or implant analog.

In the shown embodiment, the top part TP is preferably made of a polymer comprising a substantial amount of PEEK, most preferably a percentage of PEEK which will allow biocompatibility, so as to enable inter-oral use. The lower part and central parts are preferably made of titanium or alloys comprising a substantial amount of titanium.

The height h3 illustrates a total height of the scan body element above implant or implant analog, when it is mounted on the implant or implant analog. This height h3 is preferably 8-10 mm for versions to be used for inter-oral scanning. However the height h3 may be larger, e.g. 12-15 mm or even larger, for versions to be used only for scanning on an implant analog on a mould. Due to the principles according to the invention, a limited height h3 is possible and still with a high scanning precision.

Figure 3A:
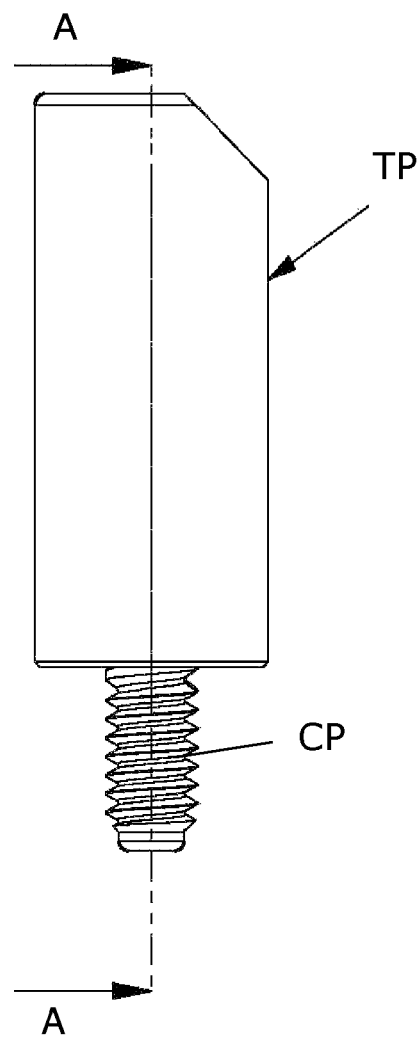
FIGS. 3a and 3b illustrate two views of a scan body embodiment with a male interface.
Figure 3B:
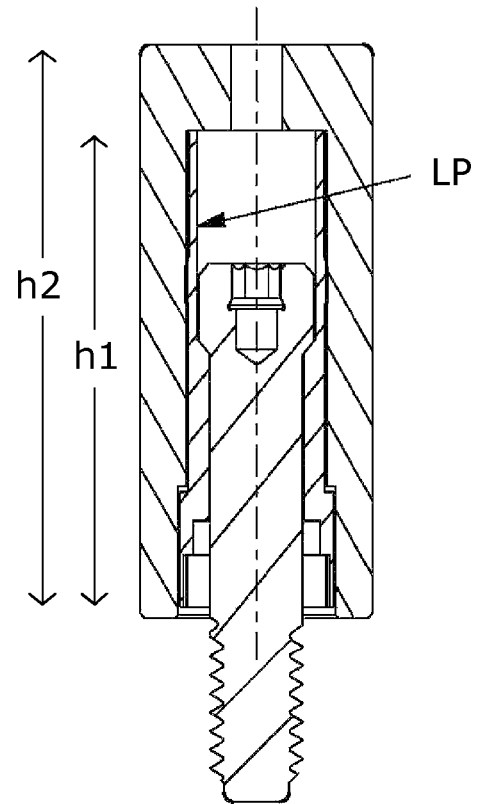

FIGS. 3a and 3b show similar views as FIGS. 2a and 2b, but for a scan body embodiment suited for mounting on an implant or implant analog with a male interface, i.e. with a protrusion arranged to engage with the bottom part of the lower part LP of the scan body element, which in this embodiment does not protrude. Rather, in the embodiment on FIGS. 3a and 3b the lower part LP is fully surrounded by the top part TP. Thus, the engaging interface between implant or implant analog and the lower part LP is also surrounded by the top part TP. When pressed to its extreme upper position, the central part CP will also be fully surrounded by the top part TP, thus enabling the lower part LP to engage with the implant or implant analog before the thread of the central part CP is turned.

As seen in this embodiment, the lower part LP extends a distance h1 inside the top part TP which exceeds 70% of a total height h2 of the top part TP. This percentage may be even higher, e.g. up to 80%, up to 90%, or even higher. Again, it is preferred, that the lower part LP extends upwardly such that it surrounds the upper part of the central part CP when it is pressed upwardly to a degree ensuring that the lower part LP can engage with the implant or implant analog interface without the central part CP having to be turned, thus facilitating practical mounting on the implant or implant analog.

Figure 4A:
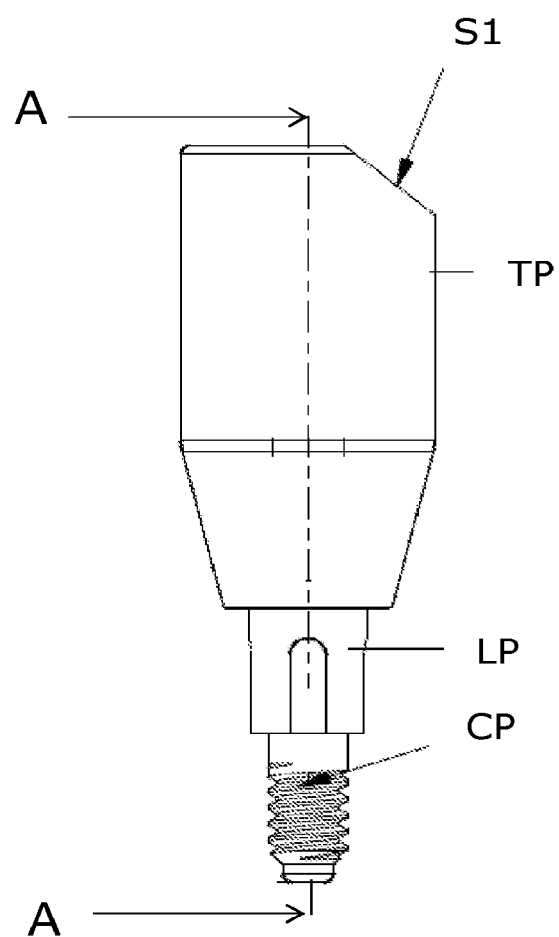
FIGS. 4a and 4b illustrate two views of a scan body embodiment suited for mounting on an implant with a female or male interface.
Figure 4B:
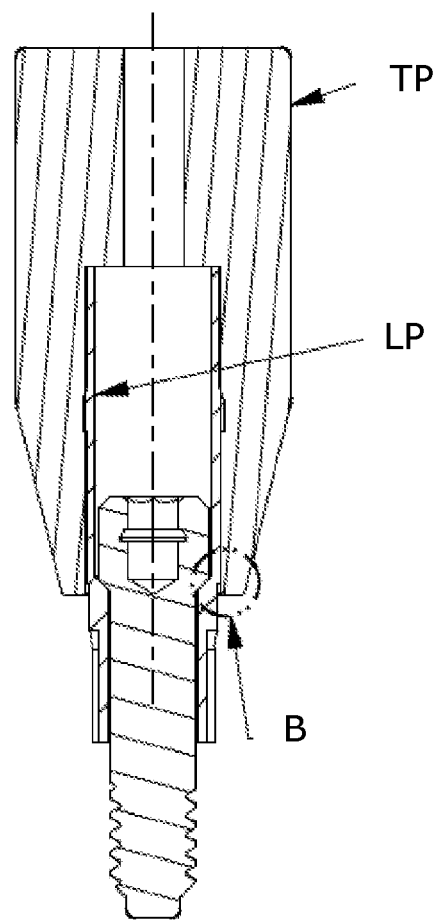
Figure 4C:
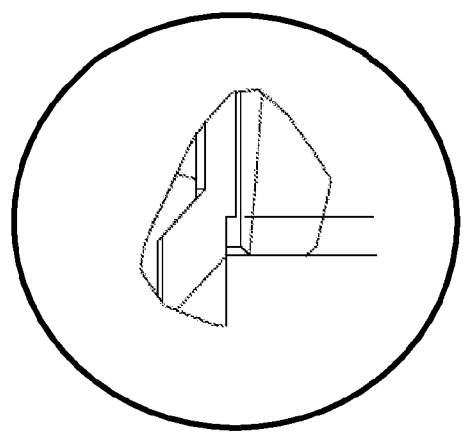
FIG. 4c is a detail view of section 'B' of the scan body embodiment shown in FIG. 4b.

FIGS. 4a, 4b and 4c shows a further embodiment of a scan body element. The basic function of the top part TP, the lower part LP, the central part CP, and the recognizable surface S1 has already been described above. A part of the surface of the top part TP on this embodiment, is bevelled to form a tapered section over at least a section of the top part TP surrounding the lower part LP. This is advantageous for inter-oral use, as there is limited space in the mouth of the user and a reduction in volume of the scan body element will improve the comfort of the patient provided with the implant.

The central part CP is, as explained above, provided with external threads. However, as can be seen, is it conceivable to limit the extent of the threads so that the central part CP has a plane surface in the interface between the central part CP and the lower part LP.

FIG. 4c shows section B in FIG. 4b. The top part TP can be provided with an inner flange at the end surface enveloping the lower part LP. The flange will provide a further precaution in view of a tight fit between the top part and the lower part. To sum up, the invention provides a scan body element to be inserted in a dental implant or implant analog for scanning in, or with, an optical scanning system. The scan body element has a polymer or a ceramic top part TP with at least one geometric feature S1 recognizable in the scanning. A metallic lower part LP is shaped to fit to a dental implant or an analog, and fixed to the top part TP, e.g. by press fitting. A central part CP is arranged inside the lower part LP, and comprises a threaded portion, and a recess R for receiving a screw driver through a hole in the top part SDO, thus allowing the threaded portion to be turned relative to the lower part LP to fasten the scan body element to the implant or the analog. The central part CP may be interlocked between the lower part LP and the top part TP and thus the scan body element constitutes one single element for normal use.

Although the present invention has been described in connection with the specified embodiments, it is not intended to be limited to the specific form set forth herein. Rather, the scope of the present invention is limited only by the accompanying claims. In the claims, the term "comprising" or "including" does not exclude the presence of other elements. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

ANNEX I

In another aspect, the invention relates to the following embodiments:
1. A scan body element insertable in, or on, a dental implant, or in, or on, an implant analog, and recognizable in an optical scanning system arranged for finding orientation and position of the scan body element, the scan body element comprising:

a top part (TP) comprising at least one geometric feature (S1) recognizable in the optical scanning system, the top part (TP) being made of a non-metal material, such as a polymer or a ceramic, a lower part (LP) made of a metal or metal alloy and shaped to fit to a dental implant or an implant analog, wherein the lower part (LP) is fixed to the top part (TP), and a central part (CP) arranged in a central opening of the lower part (LP), wherein the central part (CP) comprises a threaded portion, and a recess (R) for receiving a screw driver through the top part (SDO), so as to allow the threaded portion to be turned relative to the lower part (LP) in order to fasten the scan body element to the dental implant or the implant analog.

2. Scan body element according to embodiment 1, wherein the top part (TP) and the lower part (LP) comprise openings (SDO) arranged for insertion of a screw driver, so as to allow the screw driver to be received in said recess (R) of the central part (CP).

3. Scan body element according to embodiment 1 or 2, wherein the central part (CP) is displaceable relative to the lower part (LP) along a longitudinal axis (LA).

4. Scan body element according to any of the preceding embodiment, wherein the top part (TP) is locked in position relative to the lower part (LP) by means of at least one of:
one or more exterior protrusions (P) on the lower part (LP) arranged for being press fitted inside the top part (TP),
by means of glue,
by means of co-moulding,
by means of corresponding threads on the top part (TP) and the lower part (LP), and
by means of a shrinking process.

5. Scan body element according to any of the preceding embodiment, wherein the top part (TP) is a solid polymer element, and wherein the lower part (LP) is fixed to the top part (TP) by means of at least one circumferential protrusion on the lower part (LP).

6. Scan body element according to any of the preceding embodiment, wherein the top part (TP), the lower part (LP) and the central part (CP) are assembled together so as to constitute one single element when fastening the element to the implant or the implant analog.

7. Scan body element according to any of the preceding embodiment, wherein the top part (TP) has an optical scanning recognizable portion with respect to an angular position by having a cross-sectional planar first surface (S1) with respect to the longitudinal axis (LA) of the scan body element.

8. Scan body element according to any of the preceding embodiment, wherein the top part (TP) surrounds an upper portion of the lower part (LP).

9. Scan body element according to embodiment 8, wherein a length (h1) of the upper portion of the lower part (LP) being surrounded by the top part (TP) is at least 20% of an outer height (h2) of the top part (TP), such as at least 30%, such as at least 40%, such as at least 50%, such as at least 60%, such as at least 70%, such as at least 80%, such as at least 90%.

10. Scan body element according to any of the preceding embodiments, wherein a total outer height (h3) of the scan body element above the implant or implant analog is below 15 mm, when the scan body element is mounted on the implant or implant analog.

11. Scan body element according to any of the preceding embodiment, wherein the lower part (LP) surrounds an upper portion of the central part (CP).

12. Scan body element according to any of the preceding embodiment, wherein an inner surface of the lower part (LP) and an outer surface of the upper portion of the central part (CP) are shaped such that the central part (CP) provides a self-centering effect upon being screwed onto the implant or implant analog.

13. Scan body element according to any of the preceding embodiment, wherein the top part (TP) is made of one of:
a polymer comprising PEEK,
a ceramic,
Teflon®, and
POM.

14. Scan body element according to any of the preceding embodiment, wherein the lower part (LP) is made of a metal or an alloy comprising at least one of: Ti, Zr, and steel.

15. Scan body element according to any of the preceding embodiment, being made from bio-compatible materials and arranged for inter-oral use.

The invention claimed is:

1. A scan body element insertable in or on a dental implant, or insertable in or on an implant analog, and recognizable in or with an optical scanning system arranged to permit determining orientation and position of the scan body element, the scan body element comprising:

a top part comprising at least one geometric feature being an angled planar surface recognizable in the optical scanning system, a lower part made of a metal or metal alloy and shaped to fit to the dental implant or the implant analog, the lower part being fixed to the top part, the lower part engaged with an inner portion of the top part via a press-fit connection formed by an interference fit between an upper portion of the lower part and a lower portion of the top part, wherein the lower part includes at least one circumferential protrusion that engages with the inner portion of the top part, and a central part arranged in a central bore of the lower part, the central part comprising a threaded portion and a first end with a recess configured to receive a screw driver through the top part such that the threaded portion is turnable relative to the lower part so as to fasten the scan body element to the dental implant or the implant analog, wherein the top part comprises an opening, and said opening of the top part and said central bore of the lower part are arranged for insertion of a screw driver such that the screw driver is received in the recess of the central part, wherein the top part is a solid polymer element, and the lower part is fixed to the top part by the at least one circumferential protrusion, wherein the top part, the lower part and the central part are assembled together so as to form a single element, wherein said central part is interlocked between the lower part and the top part, and wherein said opening of said top part is smaller than said first end of said central part.

2. The scan body element according to claim 1, wherein the central part is displaceable relative to the lower part along a longitudinal axis.

3. The scan body element according to claim 1, wherein the top part surrounds the upper portion of the lower part.

4. The scan body element according to claim 3, wherein a length of the upper portion of the lower part being surrounded by the top part is at least 20% of an outer height of the top part.

5. The scan body element according to claim 1, wherein the lower part surrounds an upper portion of the central part.

6. The scan body element according to claim 1, wherein an inner surface of the lower part and an outer surface of an upper portion of the central part are shaped such that the central part provides a self-centering effect upon being screwed onto the implant or implant analog.

7. The scan body element according to claim 1, wherein the scan body element comprises bio-compatible materials and is configured to be inserted inter-orally.

8. The scan body element according to claim 1, wherein the lower part is formed of a metal or an alloy comprising at least one of Ti, Zr, and steel.

9. The scan body element according to claim 1, wherein the at least one geometric feature is disposed on an outermost surface of the top part.

10. A scan body element insertable in or on a dental implant, or insertable in or on an implant analog, and recognizable in or with an optical scanning system arranged to permit determining orientation and position of the scan body element, the scan body element comprising:
   a top part comprising at least one geometric feature being an angled planar surface recognizable in the optical scanning system, the top part comprising a non-metal material,
   a lower part comprising a metal or metal alloy and shaped to fit to the dental implant or the implant analog, the lower part being fixed to the top part, the lower part engaged with an inner portion of the top part via a press-fit connection formed by an interference fit between an upper portion of the lower part and a lower portion of the top part, wherein the lower part includes at least one circumferential protrusion that engages with the inner portion of the top part, and
   a central part arranged in a central bore of the lower part, the central part comprising a threaded portion and a recess configured to receive a screw driver through the top part such that the threaded portion is turnable relative to the lower part so as to fasten the scan body element to the dental implant or the implant analog,
   wherein the top part comprises an opening, and said opening of the top part and said central bore of the lower part are arranged for insertion of the screw driver such that the screw driver is received in the recess of the central part,
   wherein the top part, the lower part and the central part are assembled together so as to form a single element,
   wherein the central part is interlocked between the lower part and the top part, and
   wherein the central part is limited in displacement relative to the lower part along a longitudinal axis.

11. The scan body element according to claim 10, wherein the top part is locked in position relative to the lower part by at least one of:
   glue,
   co-molding,
   corresponding threads on the top part and the lower part, and
   a shrinking process.

12. The scan body element according to claim 10, wherein the top part is a solid polymer element, and the lower part is fixed to the top part by the at least one circumferential protrusion on the lower part.

13. The scan body element according to claim 10, wherein the top part comprises one of: a polymer comprising PEEK, a ceramic, Teflon®, and POM.

14. The scan body element according to claim 10, wherein the top part includes an optical scanning recognizable portion being said at least one geometric feature disposed relative to an angular position and having a cross-sectional planar first surface arranged with respect to the longitudinal axis of the scan body element.

15. A scan body element insertable in or on a dental implant, or insertable in or on an implant analog, and recognizable in or with an optical scanning system arranged to permit determining orientation and position of the scan body element, the scan body element comprising:
   a top part comprising at least one geometric feature being an angled planar surface recognizable in the optical scanning system, the top part comprising a non-metal material,
   a lower part comprising a metal or metal alloy and shaped to fit to the dental implant or the implant analog, the lower part engaged with an inner portion of the top part via a press-fit connection formed by an interference fit between an upper portion of the lower part and a lower portion of the top part, wherein the lower part includes at least one circumferential protrusion that engages with the inner portion of the top part so as to fix the lower part to the top part, and
   a central part arranged in a central bore of the lower part, the central part comprising a threaded portion and a recess configured to receive a screw driver through the top part such that the threaded portion is turnable relative to the lower part so as to fasten the scan body element to the dental implant or the implant analog,
   wherein the top part comprises an opening, and said opening in the top part and said central bore of the lower part are arranged for insertion of the screw driver such that the screw driver is received in the recess of the central part,
   wherein the top part, the lower part and the central part are assembled together so as to form a single element,
   wherein an opening of said top part is smaller than said central bore of said lower part,
   wherein the top part surrounds the upper portion of the lower part,
   wherein said central part is interlocked between the lower part and the top part, and
   wherein said central part is displaceable relative to the lower part along a longitudinal axis.

16. The scan body element according to claim 15, wherein a length of the upper portion of the lower part being surrounded by the top part is at least 20% of an outer height of the top part.

17. The scan body element according to claim 15, wherein a total outer height of the scan body element above the implant or the implant analog is below 15 mm, when the scan body element is mounted on the implant or the implant analog.

18. The scan body element according to claim 15, wherein the lower part surrounds an upper portion of the central part.

* * * * *